United States Patent

Close et al.

[11] 4,056,573
[45] Nov. 1, 1977

[54] SYNTHESIS OF ACYCLIC, TERPENE ALCOHOLS

[75] Inventors: Ralph E. Close; John M. Derfer, both of Jacksonville, Fla.

[73] Assignee: SCM Corporation, New York, N.Y.

[21] Appl. No.: 701,699

[22] Filed: July 1, 1976

Related U.S. Application Data

[63] Continuation-in-part of Ser. No. 571,375, April 24, 1975, abandoned.

[51] Int. Cl.$^2$ .................. C07C 29/00; C07C 41/00
[52] U.S. Cl. .................. 260/631.5; 252/522; 260/615 R; 560/249
[58] Field of Search ............ 260/631.5, 615 R Primary Examiner—Joseph E. Evans
Attorney, Agent, or Firm—Richard H. Thomas

[57] ABSTRACT

Shown is a process for the synthesis of acyclic, terpene alcohols, such as 3,7-dimethyloctan-1-ol and 7-substituted hydroxy or ethoxy derivatives thereof, wherein 3-methylbut-1-yn or the 3-substituted hydroxy or ether derivative thereof is coupled with a $C_5$ coupling reagent having the configuration,

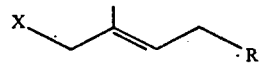

X being a leaving group such as chloride, bromide, iodide, tosylate and mesylate; R being

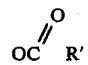

or OR', R' being a lower alkyl up to 5 carbon atoms, phenyl, substituted phenyl up to 10 carbon atoms, cycloalkyl or aralkyl up to 10 carbon atoms, followed by hydrogenation and saponification or deetherification.

8 Claims, No Drawings

SYNTHESIS OF ACYCLIC, TERPENE ALCOHOLS

This application is a continuation-in-part of prior application, now abandoned, Ser. No. 571,375, filed April 24, 1975, and entitled "Synthesis of Hydroxycitronellol."

The present invention relates to the synthesis of certain acyclic, terpene alcohols. It will be described with particular reference to the synthesis of hydroxycitronellol which has the formula and structure as follows:

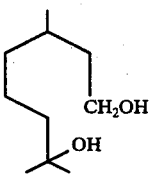

3,7-dimethyloctan-1, 7-diol although it will be apparent to those skilled in the art that the present invention has other applications as well.

BACKGROUND OF THE INVENTION

Alcohols, the syntheses of which are within the scope of the present invention, include hydroxycitronellol, 3,7-dimethyloctan-1-ol, and such ether alcohols as methoxy citronellol (7-methoxy-3,7-dimethyloctan-1-ol).

A primary use for hydroxycitronellol is as an intermediate in the synthesis of hydroxycitronellal, (7-hydroxy-3,7-dimethyloctan-1-al), a widely used perfumery material. Conventionally, in this synthesis, a mixture of geraniol and nerol is prepared from beta-pinene via myrcene hydrochloride and is partially hydrogenated to produce citronellol. Citronellol is then hydrated under acid conditions to produce hydroxycitronellol. It has also been made from myrcene by preparing the dihydrochloride and then chlorodihydrogeranyl acetate, followed by saponification and hydrogenation.[1]

[1]. Perfume and Flavor Chemicals, Steffen Arctander, 1969, Vol. 1, 1737.

A primary problem with these routes to hydroxycitronellol is that they depend upon the availability of beta-pinene as a precursor for myrcene, and beta-pinene is in relatively short supply.

It is known to couple methylbutynol (3-methylbut-1-yn-3-ol) with certain allylic halides in an aqueous media in the presence of cuprous chloride and a base, the latter being either organic or inorganic. Yields range from 50 to 70% depending upon the allylic halide and the type of base used.

Methylbutynol, however, like all other acetylenes, has its own specific requirements for coupling. These are dependent on the nature of the particular coupling reactant, solvent employed, the method of forming the cuprous derivative, the presence of coordinating agents which can activate the cuprous acetylide, and many other factors. To Applicants' knowledge, no attempt has heretofore been made to couple methylbutynol with a compound such as isoprene chloroacetate (1-chloro-4-acetoxy-2-methyl-2-butene).

Copending application Ser. No. 560,550, filed Mar. 20, 1975 by William Oroshnik and Ralph E. Close, assigned to Assignee of the present application (identified as case No. I-1881) describes a process for the production of dehydrophytol and Vitamin E wherein hexahydropseudoionone is reacted with a metal acetylide in a condensation reaction to form the corresponding $C_{15}$ acetylenic carbinol, which in turn through a series of reactions is coupled with isoprene chloroacetate to form a $C_{20}$ acetoxy enyne. The latter by a further series of hydrogenation and saponification reactions forms the compound dehydrophytol. This in turn couples with trimethylhydroquinone to give dehydro-Vitamin E which is then hydrogenated to give Vitamin E. The disclosure of copending application Ser. No. 560,550 (case I-1881), is incorporated by reference herein.

In addition to the use of hydroxycitronellol as an intermediate for the production of hydroxycitronellal, the alcohol also is used in perfume compositions with the intention of stabilizing the hydroxycitronellal and prolonging the odor life of that aldehyde in compositions. The alcohol also has other uses.

Dimethyloctanol (3,7-dimethyloctan-1-ol) is also useful as an intermediate in the preparation of perfumery compositions and as an intermediate in the synthesis of juvenile hormones. Similarly, the ether derivatives of dimethyloctanol such as methoxy citronellol find use in the perfumery art and as intermediates in the synthesis of juvenile hormones.

SUMMARY OF THE INVENTION

The present invention resides in the discovery that a $C_5$ acetylene compound, such as 3-methylbut-1-yn or the 3-substituted hydroxy or ether counterpart thereof can readily be coupled with a $C_5$ coupling reagent having the general configuration

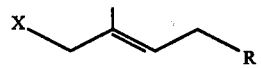

wherein X is a leaving group such as chloride, bromide, iodide, tosylate and mesylate, R being

or OR', R' being a lower alkyl up to 5 carbon atoms, phenyl, substituted phenyl up to 10 carbon atoms, cycloalkyl or aralkyl up to 10 carbon atoms, in a coupling reaction to form a $C_{10}$ enyne, which then can be subjected to hydrogenation and saponification or deetherification, or vice versa, to form the compounds 3,7-dimethyloctan-1-ol, hydroxycitronellol or the 7-substituted ether counterpart thereof, respectively. The invention also resides in the discovery of conditions by which the above coupling reaction is accomplished. In particular, the reaction is carried out in the presence of an acid scavenger and solvent employing a cuprous salt as a catalyst.

The synthesis of hydroxycitronellol by the concepts of the present invention can be represented in the following series of equations:

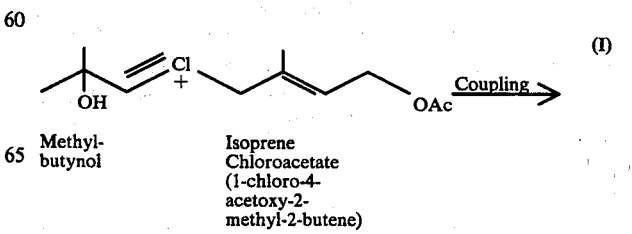

Methyl-
butynol

Isoprene
Chloroacetate
(1-chloro-4-
acetoxy-2-
methyl-2-butene)

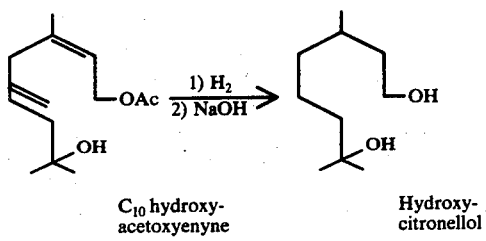

C₁₀ hydroxy-
acetoxyenyne                Hydroxy-
                            citronellol The syntheses of 3,7-dimethyloctan-1-ol and the 7-substituted ether counterparts thereof may be represented by the following series of equations:

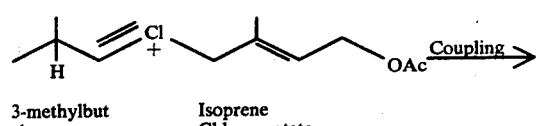

(II)

3-methylbut-1-yn    Isoprene
                    Chloroacetate

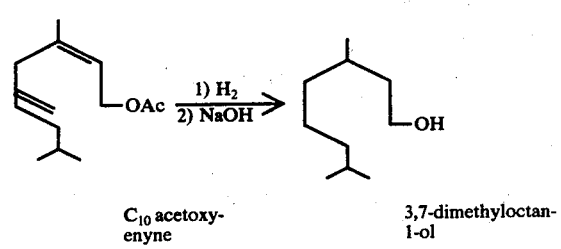

C₁₀ acetoxy-           3,7-dimethyloctan-
enyne                  1-ol

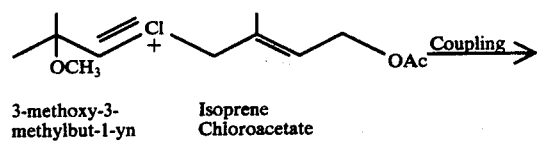

3-methoxy-3-        Isoprene
methylbut-1-yn      Chloroacetate

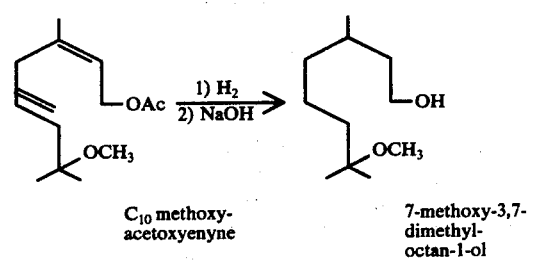

C₁₀ methoxy-           7-methoxy-3,7-
acetoxyenyne           dimethyl-
                       octan-1-ol A principal advantage of the present invention lies in the ready availability of methylbutynol and its cost. The compound 3-methylbut-1-yn (equation II) is readily prepared from methylbutynol by standard conversion via halides and tosylates. Similarly, the ether derivatives (equation III) are readily prepared from methylbutynol by conventional etherification methods such as with dimethylsulfate in the presence of a base catalyst.

In the above reaction sequences, the leaving group on the C₅ coupling reagent (the isoprene chloroacetate) can be other than chloride; for instance any halide such as iodide, bromide, or tosylate or mesylate, all well-known leaving groups. Similarly, the substitution in the 4-position of the isoprene chloroacetate need not be an acetate. The group can be any ester of the configuration

wherein R' is as previously described. Alternatively, the substitution can be by an ether group having the configuration OR', R' being again as previously described.

In the case where the substitution is with an ester, the alcohol is obtained by simple saponification. Alternatively, where the substitution is with an ether, a simple deetherification procedure may be employed, for instance as follows:

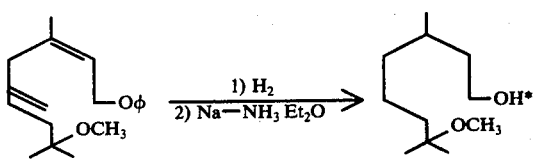

*Note:
Journal of the American Chemical Society, 57, 603, (1937)
Journal Organic Chemistry, (1965), 30, page 1610 and (1971), 36, page 2035, the disclosures of which are incorporated by reference herein.

There has been substantial literature written generally about the coupling of acetylenes with halides. In the book *Chemistry of Acetylenes* by H. G. Viehe, Marcel Dekker, New York, 1969, pages 630-633, Cadiot et al describe this coupling including the reaction of acetylenes with allylic halides. On page 630, they report:

"These rapid reactions are carried out at room temperature mostly in a hydrophilic medium (water, ethanol, etc.). Cuprous chloride is employed in catalytic amounts (1-2% or more).

Although these halides are not oxidizing, some hydroxylamine salt may be added to prevent any cuprous ion air oxidations. A base is necessary to neutralize the generated hydracid. With mineral bases relatively hard reaction conditions are necessary, while in the presence of certain amines these condensations become rather rapid, because of the influence of amines as complexing agents in the cuprous derivative formation process. Ammonia primary amines and hydroxylamine are of particular interest.

The solvents employed are similar to those required for Cadiot-Chodkiewicz coupling. Better yields are observed with chlorides and tosylates than with the corresponding bromides and iodides. This reaction seems to be limited to the hydrophilic acetylenes and good results are obtained especially with acetylenic alcohols."

Also in a book by Thomas F. Rutledge, "Acetylenic Compounds. Preparation and Substitution Reactions," Reinhold Book Corporation, 1968, pages 94, 95, the catalytic reaction of allylic chlorides with acetylenes is described.

"Only 1-2% of the cuprous salt was enough to catalyze the reaction. Water, alcohol and dimethyl sulfoxide were good solvents. Since the reaction liberates an acid, a base is necessary; primary amines lead to faster rates than secondary or tertiary amines. Some bases directed the propargylic alcohol-propargyl bromide reaction to the allenyne (Table 4-22). The directive effect of bases depended on the propargylic halide. Ammonium hydroxide was the most effective. The reaction of methylbutynol with propargyl chloride gave 80% yield of allenyne in the presence of ammonium hydroxide. Propargyl chloride gave the highest yield, followed by the tosylate, bromide and iodide."

A number of bases are listed by Rutledge, including sodium hydroxide, ammonium hydroxide, ethylamine, diethylamine, triethylamine, t-butylamine, heterocyclic amines such as pyridine, and others.

In the publication Justus Liebigs *Annalen der Chemie*, 658, 1962, pages 6-20, Kurtz on page 19 describes the synthesis of 1-heptene-4-eyne-ol-6 from methylbutynol and allyl chloride employing concentrated hydrochloric acid and cuprous chloride in an aqueous medium. A base is employed (in this instance, sodium chloride) to maintain a pH of about 7.5-8.5. The reaction is carried out at 60° C. to give a yield of about 85% heptene.*

* The relevant disclosures of Viehe, Rutledge and Kurtz are incorporated by reference herein.

In the present invention, involving the reaction of a $C_5$ acetylenic compound such as methylbutynol with a $C_5$ allylic coupling reagent, the use of a cuprous salt is critical, although to Applicants' knowledge, any cuprous salt can be employed. Satisfactory results were achieved with cuprous halides such as CuCl, but the present invention in its broadest aspects includes the use of other cuprous salts. It might be possible to employ silver and gold salts, but these compounds are too expensive. The salt may be employed in catalytic amounts, e.g., about 1-2% or more, although best yields are obtained with the use of greater amounts, e.g., stoichiometric amounts. The reaction of the present invention is carried out in a solvent which may be aqueous or non-aqueous. In the case where the solvent is non-aqueous, aprotic solvents wuch as tetrahydrofuran (THF), N,N-dimethylacetamide (DMA), n-methylpyrrolidene, hexamethylphosphoramide (HMPA) and dimethylsulfoxide (DMSO) give good yields.

The acid scavenger can be any of a number of bases. In the case where an aqueous medium is employed, the acid scavenger acts as a buffering agent to buffer the acid liberated in the reaction. Suitable buffering agents may be sodium chloride, shown by Kurtz, sodium acetate, sodium phosphate, calcium oxylate and others well known to those skilled in the art. The purpose of the buffering agent is to maintain a relatively constant pH in the reaction medium, and sufficient buffering agent is added to accomplish this. In the case where the solvent is non-aqueous, the acid scavenger can be thought of as reacting with the hydra acid formed by the leaving group and hydrogen. The base should be soluble in the non-aqueous medium, but again, can be any of a number of compounds, for instance those listed by Rutledge. Although the present invention in its broadest respect is not limited to particular bases, good results were achieved employing primary amines such as t-butylamine and other lower alkyl amines such as diisopropylethylamine (Honig's base). The base, of course, is employed in a stoichiometric amount.

The reaction should be carried out in a manner to prevent oxidation of the cuprous ion. Preferably, this is accomplished with a nitrogen atmosphere, but use of a reducing compound such as the hydroxylamine salt disclosed by Cadiot et al is possible. Temperature is not important. The reaction was found to be slightly exothermic and some cooling is employed.

The following examples illustrate the present invention, the first example being an illustration of the reaction carried out in a non-aqueous medium, the second example being an illustration of the reaction carried out in part in an aqueous medium. In both instances, approximately stoichiometric amounts of cuprous salt were employed, although this is not essential. In the first example, the acid scavenger is t-butylamine, functioning as a hydrogen halide acceptor. In the second example, the base is sodium acetate functioning more as a buffering agent, although in this example, the copper complex of the base, copper ion and acetylene first was formed in the aqueous medium, but the actual coupling with $C_5$ coupling reactant was carried out in an organic solvent. The reactions of both examples were carried out with isoprene chloroacetate as the coupling reagent, although as indicated above, the $C_5$ allyl reagent can have any halide such as chloride, bromide and iodide as the leaving group, as well as tosylate or mesylate. In place of the acetate group, again, any ester or ether group may be employed, R' of the group being as previously defined.

It should be noted that a heterocyclic amine such as pyridine when employed as the acid scavenger can also function as the solvent (notice page 630 of Cadiot et al).

The present invention will become more apparent from the following examples. In these examples, temperatures are in degrees Centigrade and percentages are by weight unless otherwise specified.

EXAMPLE 1

In this example, the following components were employed:

| | | |
|---|---|---|
| 3-Methylbut-1-yn-3-ol | 2.14 g. (0.0255 mol) | |
| CuCl | 2.48 g. (0.0250 mol) | |
| t-$C_4H_9NH_2$ | 1.83 g. (0.0250 mol) | 2,63 ml. |
| Isoprene chloroacetate | 3.25 g. (0.020 mol) | |
| DMF | 9.0 ml. | |

A 50 milliliter 3-necked flask was equipped with a magnetic stirrer, a thermometer and a nitrogen inlet tube to maintain a blanket of nitrogen over the reaction mixture throughout the process. The CuCl and 3 ml. of the DMF (dimethylformamide) were added to the flask and stirred. During stirring, a solution of the acetylene (3-methylbut-1-yn-3-ol) in 3 ml. of DMF was added. The reaction was exothermic and was kept at 40°-50° with a cooling bath. The CuCl went completely into solution, and at this point, the solution was then cooled to 30° and the t-butylamine was added. Again, the temperature rose to 40°-50°, at which time it was stirred for about 10-15 minutes and cooled to 30°. The amine coordinates with the acetylene-copper derivative and acts as an HCl scavenger.

The isoprene chloroacetate in 3 ml. of DMF was then added. Again there was a small exothermic effect (5°-7°) during the course of an hour. The solution was stirred overnight at room temperature (total time about 20 hrs.) and was quenched with 50 ml. dilute ammonium hydroxide ($NH_4OH$) and extracted with ether.

The ether extract was washed three times with 1 M HCl (50 ml.) and then once with 10% sodium bicarbonate ($NaHCO_3$ — 50 ml.) and dried with sodium sulfate ($Na_2SO_4$). It was then filtered and concentrated under vacuum to give 3.3 grams or a 79% yield of a pale yellow oil.

Of this oil, 67% was the desired $C_{10}$ enyne or hydroxy acetate product, as determined by gas-liquid chromatography.

The product can be named 1-acetoxy-7-hydroxy-3,7-dimethylocta-2-ene-5-yne.

Three grams of the above crude product was distilled through a short path Claisen still at 0.02 mm. to give the following fractions I and II:

| | | | |
|---|---|---|---|
| I | 65–76° | 0.6 g. GLC - B - - C - | $n_D^{25}$ 54.4% 34.4% | 1.4670 |
| II | 76–79° | 1.7 g. GLC - B - - C - | $n_D^{25}$ 11.1% 84.2% | 1.4729 |

GLC analysis of the two fractions indicated that fraction I contained 54.4% cyclopentadiene by-product (1-methyl-4-(1-methyl-1-hydroxyethyl)-5-acetoxymethyl-1,3-cyclopentadiene) and 34.4% of the desired $C_{10}$ hydroxy-acetate coupling product; whereas fraction II contained 11.1% cyclopentadiene by-product and 84.2% of the desired $C_{10}$ hydroxy-acetate coupling product.

Isoprene chloroacetate (1-chloro-4-acetoxy-2-methyl-2-butene) is a known compound and is prepared by the chlorohydronation of isoprene in glacial acetic acid as described in an article by W. Oroshnik and R. A. Mallory, Journal of Amer. Chem. Soc., 72, 4608 (1950). Alternatively, the isoprene chloroacetate may be prepared by the method described in copending application Ser. No. 359,011, filed May 10, 1973, by Carlos G. Cardenas, assigned to Assignee of the present application and now U.S. Pat. No. 4,001,307.

EXAMPLE 2

In this example, the following components were reacted:

| | |
|---|---|
| 3-Methylbut-1-yn-3-ol | 1.87 g. (0.0223 mol) |
| CuCl | 1.98 g. (0.020 mol) |
| NH$_4$Cl (saturated aqueous) | 20 ml. |
| NaOAc (saturated aqueous) | 6 ml. |

The cuprous chloride and the ammonium chloride were mixed under nitrogen. The NaOAc was then added to give a solution having a pH of 6. The latter was filtered under nitrogen to remove suspended material, and the methylbutynol (1.87 g.) was added to the resulting clear colorless solution. This gave an intermediate yellow solution which was allowed to stand under nitrogen. After several hours, precipitation commenced.

At the end of several days, the product was filtered on a Buchner funnel and washed with water (3 times) and then with acetone three times. It was then dried in a dessicator over calcium chloride to yield 1.76 g. of the methylbutynol copper derivative. This copper derivative (1.3 g., 0.0089 mol) in 5 ml. DMF was then coupled with 0.85 g. (0.00523 mol) isoprene chloroacetate in 5 ml. DMF. Initial mixing gave a heavy suspension. After one hour stirring under nitrogen, the heavy suspension was replaced with a smaller amount of a finely-divided solid. During this time, the temperature rose from 26° to 28°. After another hour and a half, the solution became homogeneous and assumed a yellow color. Twenty-four hours later a new precipitate was formed and the reaction was worked up as in Example 1. A crude yield of 0.87 g. (79% of theory) by GLC analysis showed a 9:1 ratio of desired $C_{10}$-hydroxy acetate to cyclopentadiene by-product.

EXAMPLE 3

This example illustrates the preparation of hydroxycitronellol from the $C_{10}$-hydroxyacetoxyenyne product of Example 1*, by hydrogenation of the acetoxyenyne followed by saponification.

* The crude Fraction II product of Example 1.

In the hydrogenation step, 0.764 grams (0.00363 mol) of the hydroxy acetoxyenyne in 17 ml. methanol was subjected at one atmosphere pressure and room temperature to a total of 275 ml. of hydrogen, of which 3.1 equivalents were absorbed. The hydrogenation catalyst employed was 0.096 grams of 5% rhodium on carbon. The reaction mixture was then filtered and concentrated and the product (1-acetoxy-7-hydroxy-3,7-dimethyloctane) showed an i.r. absorption at 2.9 (—OH) and 5.75, 8.05 and 9.64 $\mu$ (OAc). Other good hydrogenation catalysts can be employed.

Saponification was then carried out with the following components:

| | |
|---|---|
| Hydroxyacetate** | 0.77 g. (0.0037 mol) |
| NaOH | 0.18 g. (0.0045 mol) |
| CH$_3$OH | 20 ml. |

After several days, the mixture was worked up by ether extraction and washing with brine, followed by drying over sodium sulfate (Na$_2$SO$_4$). The solution was filtered and concentrated, GLC analysis indicating 42.1% hydroxycitronellol.

We claim:

1. A process for the preparation of 3,7-dimethyloctan-1-ol and derivatives thereof substituted at the 7-position with an hydroxy or ether group, comprising the steps of
   a. coupling 3-methylbut-1-yn or the 3-hydroxy or ether substituted derivative thereof with a C$_5$ coupling reagent having the configuration

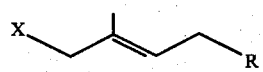

X being a leaving group selected from the group consisting of chloride, bromide, iodide, tosylate and mesylate, R being

or OR', R' being a lower alkyl up to 5 carbon atoms, phenyl, substituted phenyl up to 10 carbon atoms, aralkyl up to 10 carbon atoms or cycloalkyl up to 10 carbon atoms;
   b. said coupling being carried out in the presence of a cuprous salt and an acid scavenger;
   c. subjecting the reaction product of step a,b) to hydrogenation and saponification or ether cleavage to convert the ester or ether group in the 1-position to an hydroxyl group.

2. The process of claim 1 wherein said cuprous salt is CuCl and said acid scavenger is a primary amine, the process employing dimethylformamide as a solvent.

3. The process of claim 2 wherein said amine is t-butylamine and said C$_5$ coupling reagent is isoprene chloroacetate, the latter being coupled with 3-methylbut-1-yn-3-ol.

4. The process of claim 3 wherein approximately stoichiometric amounts of the amine, CuCl, isoprene chloroacetate and 3-methylbut-1-yn-3ol are employed.

5. A process for the preparation of hydroxycitronellol comprising a. coupling 1-chloro-4-acetoxy-2-methyl-2-butene with 3-methylbut-1-yn-3-ol in the presence of cuprous halide, a hydrogen halide acceptor and a non-aqueous medium; and
b. subjecting the reaction product of step (a) to hydrogenation and saponification.

6. A process for the preparation of hydroxycitronellol comprising
a. reacting 3-methylbut-1-yn-3-ol with cuprous halide in saturated aqueous ammonium chloride to obtain the methylbutynol copper derivative which is isolated;
b. reacting the methylbutynol copper derivative of step (a) with 1-chloro-4-acetoxy-2-methyl-2-butene in a non-aqueous medium; and
c. subjecting the reaction product of step (b) to hydrogenation and saponification.

7. The process of claim 5 wherein step (a) is carried out under a nitrogen atmosphere.

8. The process of claim 6 wherein steps (a) and (b) are carried out under a nitrogen atmosphere.

* * * * *

UNITED STATES PATENT AND TRADEMARK OFFICE
CERTIFICATE OF CORRECTION

PATENT NO. : 4,056,573
DATED : November 1, 1977
INVENTOR(S) : Ralph E. Close and John M. Derfer It is certified that error appears in the above-identified patent and that said Letters Patent are hereby corrected as shown below:

Col. 3, line 35, after the compound insert --(III)--.
Col. 5, line 29, change "wuch" to --such--. Col. 6, line 29, change "2,63 ml." to --2.63 ml.--. Col. 8, before line 22, insert --**The product of the hydrogenation step.--.

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*